United States Patent
Han et al.

(10) Patent No.: US 6,401,538 B1
(45) Date of Patent: Jun. 11, 2002

(54) METHOD AND APPARATUS FOR ACOUSTIC FLUID ANALYSIS

(75) Inventors: Wei Han, Missouri City; James Robert Birchak, Spring; Bruce H. Storm, Jr., Houston, all of TX (US)

(73) Assignee: Halliburton Energy Services, Inc., Dallas, TX (US)

( * ) Notice: Subject to any disclaimer, the term of this patent is extended or adjusted under 35 U.S.C. 154(b) by 0 days.

(21) Appl. No.: 09/655,545

(22) Filed: Sep. 6, 2000

(51) Int. Cl.$^7$ ............................................. G01N 29/02
(52) U.S. Cl. ..................... 73/599; 73/602; 73/61.75; 73/24.03; 73/19.03; 73/64.53; 73/865.5
(58) Field of Search ................ 73/61.75, 599, 73/24.03, 606, 64.53, 865.5, 19.03, 627, 28.01, 30.01, 30.03, 32 R, 32 A, 54.41, 61.45, 61.41, 61.49, 61.71, 602

(56) References Cited

U.S. PATENT DOCUMENTS

| | | | |
|---|---|---|---|
| 3,889,533 A | * 6/1975 | Balser | 73/861.21 |
| 3,914,984 A | 10/1975 | Wade | 73/61 R |
| 3,987,673 A | * 10/1976 | Hansen | 73/861.31 |
| 4,102,186 A | * 7/1978 | Brown | 73/861.31 |
| 4,162,630 A | * 7/1979 | Johnson | 73/861.31 |
| 4,317,178 A | * 2/1982 | Head | 73/861.31 |
| 4,381,674 A | 5/1983 | Abts | 73/599 |
| 4,432,243 A | * 2/1984 | Lowell et al. | 73/861.31 |
| 4,527,420 A | 7/1985 | Foote | 73/61 R |
| 4,580,444 A | * 4/1986 | Abts et al. | 73/599 |
| 4,718,269 A | * 1/1988 | Der Kindeen | 73/861.25 |
| 4,739,662 A | * 4/1988 | Foote | 73/599 |
| 5,130,950 A | 7/1992 | Orban et al. | 367/34 |
| 5,361,632 A | 11/1994 | Magnani | 73/153 |
| 5,546,812 A | * 8/1996 | Drenthen | 73/861.31 |
| 5,741,962 A | 4/1998 | Birchak et al. | 73/152.16 |
| 5,777,278 A | 7/1998 | Bednarczyk et al. | 181/102 |
| 5,969,237 A | 10/1999 | Jones et al. | 73/61.75 |

FOREIGN PATENT DOCUMENTS

| | | | |
|---|---|---|---|
| WO | WO 98/34105 | 8/1998 | H01N/29/02 |

OTHER PUBLICATIONS

Gordon S. Kino, "Acoustic Waves: Devices, Imaging, and Analog Signal Processing", Prentice Hall, Inc. Englewood Cliffs, New Jersey, 300–311 (19 ).

Zhljing Wang et al, "Acoustic Velocities in Petroleum Oils", JPT:192–200 (1990).

A.R. Smits et al, "In–Situ Optical Fluid Analysis as an Aid to Wireline Formation Sampling", SPE Formation Evaluation, 91–98, (1995).

* cited by examiner

*Primary Examiner*—Hezron Williams
*Assistant Examiner*—Rose M. Miller
(74) *Attorney, Agent, or Firm*—Marcella D. Watkins; William M. Imwalle

(57) ABSTRACT

A method is provided for analyzing suspended particulate and liquid medium in a fluid stream by transmitting acoustic signals into the fluid, detecting scattered acoustic energy, and determining a parameter related to the density and compressibility of the fluid. In one embodiment, the fluid analysis tool comprises two transmitting transducers intermittently emitting acoustic signals, and two receiving transducers being differently azimuthally positioned with respect to the transmitters. The ratio of the amplitude of scattered signals measured by the two receivers as a result of emission from the first and second transmitters are used to calculate the parameter. In another embodiment, a tool comprising one transmitter and at least three receivers with azimuthal angles in both forward and backward scattering regions with respect to the incident wave is disclosed. The scattering signal amplitudes normalized by the amplitude from one of the receivers is used to identify and monitor the system.

14 Claims, 5 Drawing Sheets

METHOD AND APPARATUS FOR ACOUSTIC FLUID ANALYSIS

RELATED CASES

Not applicable.

STATEMENT REGARDING FEDERALLY SPONSORED RESEARCH OR DEVELOPMENT

Not applicable.

TECHNICAL FIELD OF THE INVENTION

This invention relates generally to a method and apparatus for performing fluid analysis downhole in a well, and more particularly to a system for in situ determination of type and condition of formation fluids in a wellbore and for collecting downhole formation fluid samples under the original formation conditions. Still more particularly, the present invention relates to a downhole tool that uses acoustic scattering of a signal to provide qualitative measurements of the degree and nature of particulate inclusions present in the fluid sample.

BACKGROUND OF THE INVENTION

In the oil and gas industry, wireline tools perform a variety of functions, including sealing different parts of the well, electromagnetically or acoustically measuring the formation, or perforating the well casing so as to allow the entry of well fluids through the perforation. These wireline tools, so-called because they are lowered into the well on a long cable or "wire," also include formation testing tools that monitor formation pressures, obtain formation fluid samples and obtain other measurements that are used for predicting reservoir performance. Wireline formation testing tools typically include an elongated body with a packer or sealing element that is used to seal the zone of interest in the wellbore, so that formation fluid samples from that zone can be received into storage chambers in the tool or passed through a downhole measuring device.

Various types of drilling fluids are used to facilitate the drilling process and to maintain a desired hydrostatic pressure in the wellbore. These drilling fluids penetrate into or "invade" the formation to varying radial depths (referred to generally as the invaded zones) depending upon the type of formation and the type of drilling fluid. In addition, as the drilling fluid invades a stratum or layer in the formation, solids that were present in the drilling fluid are filtered out by the formation, forming a "mud cake." The liquid portion of the invading drilling fluid, known as "filtrate," thus often invades much more deeply into the formation than does the solid portion.

When it is desired to sample the formation fluid, it is necessary to ensure that both the filter cake and the filtrate have been removed from the sampled region, otherwise the sample will be contaminated with some portion of the drilling fluid. Hence, the fluid stream collected by the formation testing tools must be analyzed to determine when the formation fluid being withdrawn is substantially free of mud and mud filtrates.

For example, resistivity measurements have been applied to distinguish oil (or gas) and water and determine the proportion of each fluid phase. Optical techniques have been utilized to identify the type of formation fluid, i.e. to differentiate between oil, water and gas present in the formation fluid. Optical reflection technique is utilized to detect gas bubbles at the optical window-fluid interface. Visible and near-infrared absorption spectrometer has also been used to differentiate between crude oils, water, and drilling mud.

These prior art systems are not entirely satisfactory, however, inasmuch as interpretation of their results is difficult and often inaccurate. Systems using fluid resistivity to determine oil/water are affected by the flow dynamics and fluid salinity, which are not always available. Since resistivity measured is that of the continuous phase of the fluid in the flowline, the resistivity measurement works well for water-hydrocarbon mixtures with water as the continuous phase, but fails for mixtures with hydrocarbon as the continuous phase. A flow of alternating slugs of hydrocarbon and water produces noisy resistivity recording. The difficulty in interpreting flowline resistivity is even greater when gas is present. The resistivity measurement can not distinguish between gas and oil.

In addition, the windows of optical devices may become coated with hydrocarbons (asphaltene, paraffin) that may distort their results. The devices also suffer from small depth of penetration for opaque fluids. This reduces their accuracy in some applications. Furthermore, optical devices can detect gas bubbles located only at the surface of optical window, and provide no estimate of fluid compressibility.

For these reasons, ultrasonic signaling has been considered for fluid analysis. Like the systems described above, however, conventional acoustic fluid analysis techniques are not entirely satisfactory. Specifically, the piezoelectric devices that are suitable transducers for use in the downhole environment tend to exhibit significant response drift when subjected to large changes in temperature or pressure. Hence, conventional acoustic fluid analysis systems require frequent calibration of the instrument, particularly when temperature or pressure is highly variable. None of the prior art systems provides an effective means for using ultrasound scattering to detect and analyze gas bubbles, or fine particles, applications primarily associated with reservoir fluid sampling and analyzing.

Thus, it is an objective of this invention to provide for a formation fluid analysis system that is relatively simple, more robust than the current state-of-the-art systems and relatively accurate in differentiating between the various types of particulate and fluids to ensure that substantially uncontaminated formation fluid samples are collected. The desired system would avoid the need for calibration of the instrument over wide temperature and pressure ranges and would detect and analyze gas bubbles, fine particles, and liquid droplets in fluid samples.

SUMMARY OF THE INVENTION

The present invention addresses the above-noted deficiencies and provides a relatively simple and robust system for analyzing one or more formation fluid samples under original formation conditions using a novel acoustic cell. The present technique includes a fluid analysis method that allows identification of various suspended particulates and liquids in downhole reservoir fluids, based upon compensated acoustic scattering measurement. The suspended particulates can be solid particles, liquid droplets of a liquid that is immiscible in a continuous liquid, or gas bubbles. The continuous liquid medium can be oil, water, or any oil-based or water-based mixture. The longitudinal acoustic impedance (longitudinal speed of sound×density) of the particulate should be different from that of the carrier liquid medium. The method comprises transmitting tone-burst waves into the fluid and measuring the amplitude of signals scattered by the particulates in the fluids and received at a plurality of azimuthally positioned receivers.

The present apparatus is robust enough for downhole use, yet avoids many of the difficulties that are inherent in previous systems. For example, the present system produces results that are less difficult to characterize than resistivity measurements when flow regime or fluid salinity is unknown, and uses a system that is largely unaffected by deposition of paraffin and asphaltene, in contrast to an optical system. Unlike previously known acoustical systems, the present system uses acoustical equipment that does not require temperature dependent calibration.

In one preferred embodiment, the present fluid analysis apparatus includes two acoustic transmitting transducers positioned opposite to each other and two receiving transducers positioned at different angles on the circumference of a cylindrical conduit. The two transmitters intermittently emit tone-burst signals at a predetermined repetition time interval. The two receivers receive scattered signals from the sample. The power amplitudes measured from the two receivers as result of emission from the first transmitter and the amplitudes as result of emission from the second transmitter are used to calculate a dimensionless parameter related to the density and compressibility of the particulate and fluid medium. By comparing the calculated parameter with known values in a database, the sample can be characterized. By tracking the value of the calculated parameter over time, changes in the nature of a fluid stream can be detected.

In a second embodiment, a device comprising one transmitter and at least three receivers is disclosed. The scattering power amplitudes from the receivers normalized by the amplitude from a reference receiver as function of scattering angles are used to identify and monitor the fluid sample.

BRIEF DESCRIPTION OF THE DRAWINGS

For a more detailed understanding of the invention, reference will now be made to the accompanying Figures, wherein.

DETAILED DESCRIPTION OF THE PREFERRED EMBODIMENTS

Figure 1:
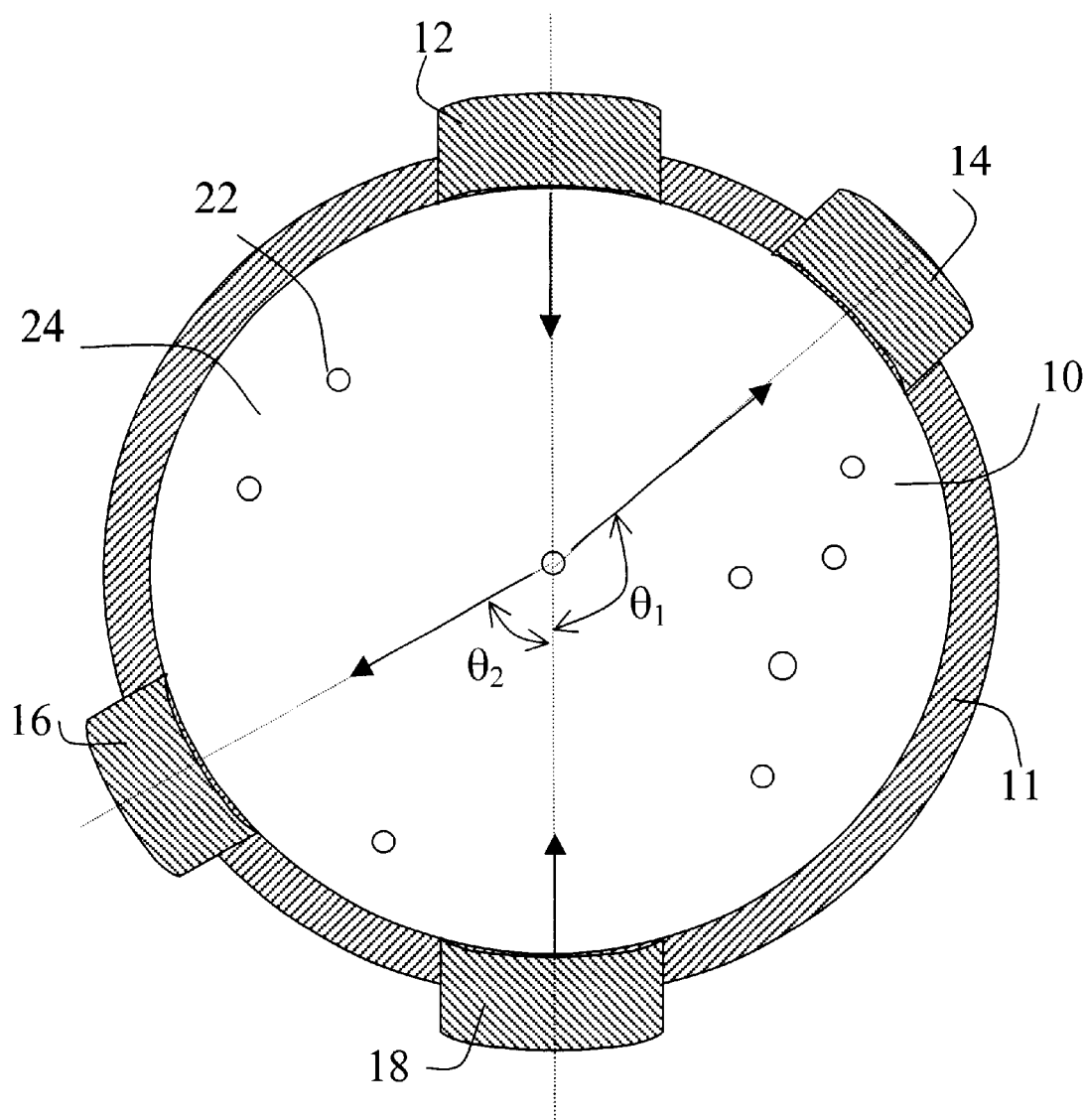
FIG. 1 is a schematic cross-section of a tool constructed in accordance with a first embodiment of the invention.

Referring to FIG. 1, a preferred embodiment of the present fluid measurement tool 10 comprises a conduit 11 having two transmitting transducers 12 and 18, and two receiving transducers 14, 16, arranged in a preferred configuration about the circumference of the conduit 11. Specifically, transmitting transducer 18 is mounted diametrically across from transmitting transducer 12. Angles $\theta_1$ and $\theta_2$ are scattering angles corresponding to the positions of receivers 14, 16 respectively. The scattering angle θ is defined herein as the angle of the scattered wave relative to the incident wave from transmitter. Hence for transmitter 12, forward scattering is defined as $0 < \theta < \pi/2$, and backscattering is defined as $\pi/2 < \theta < \pi$. Because receiving transducers 14 and 16 are preferably mounted at different azimuthal positions on the tool, angles $\theta_1$ and $\theta_2$ are not equal.

Transducers 12, 14, 16, and 18 may be in direct contact with the flowing fluid, or may be clamp-mounted outside of the conduit wall or otherwise affixed to or within conduit 11. The transducers can be focused at the center of the conduit if desired, or at some other point in the conduit. It will be understood that while the present description is presented in terms of a conduit, the present method and apparatus have equal applicability in a device that does not allow fluid flow therethrough, such as a fluid measurement chamber.

In one suitable application, the fluid flowing in conduit 11 comprises scattering particulate 22 in a continuous liquid medium 24. Liquid medium 24 can be oil, water, or any oil-based or water-based mixture. Similarly, scattering particulate 22 can be solid particles, liquid droplets, or gas bubbles.

In a preferred mode of operation, transmitters 12 and 18 each intermittently emit several cycles of tone-burst signals of frequency $f_0$ at a repetitive frequency $f_{rep}$. A preferred frequency for the driving signal ranges from 2–25 megahertz and the repetition rate range is about 10–100 kHz. After each signal transmission from either transmitter 12 or 18, receivers 14 and 16 measure the scattered signals. Time gating of the received signals can be used to allow only the scattering wave from a well-defined volume inside the conduit to be measured, as discussed below.

Figure 2:
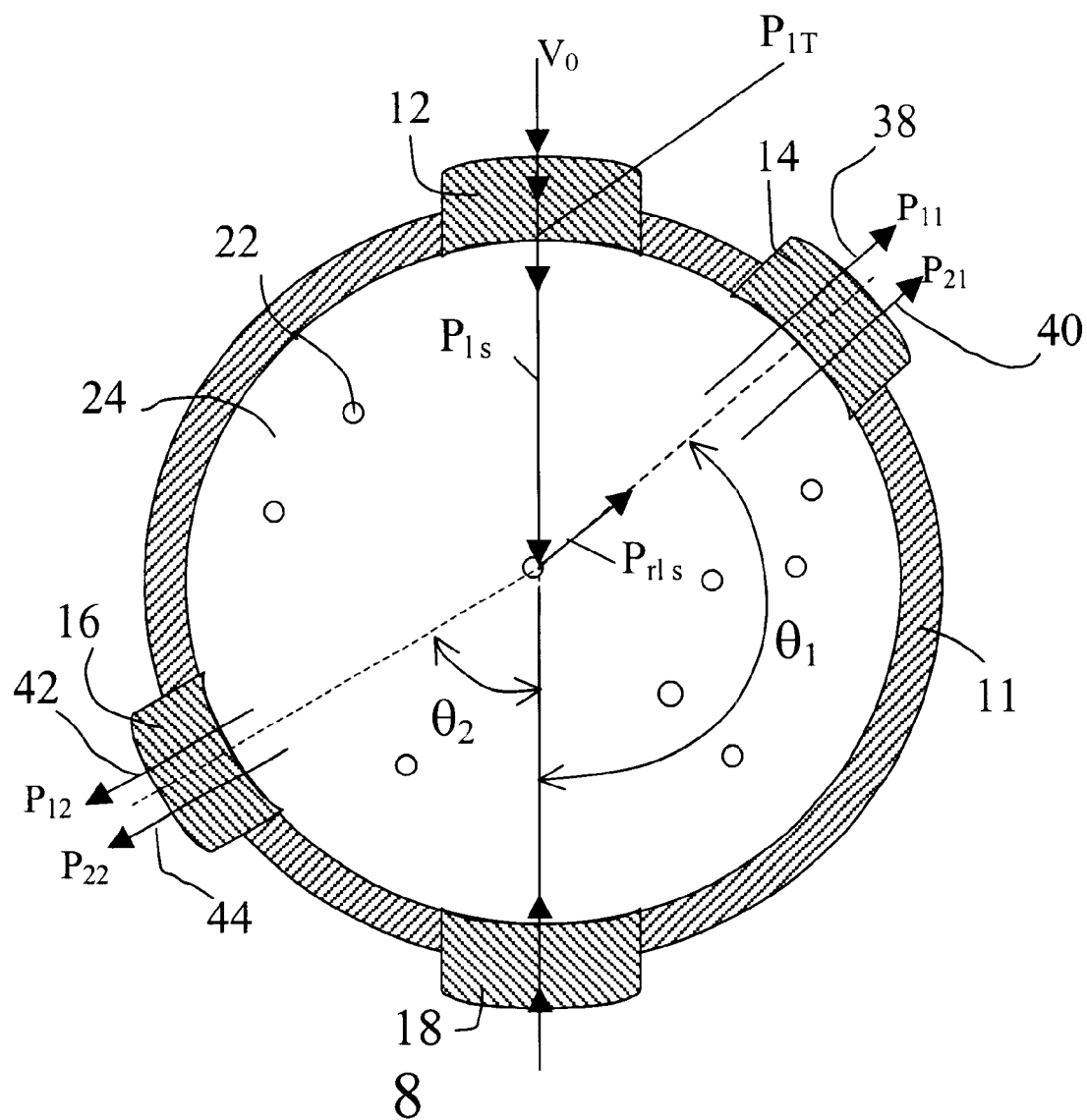
FIG. 2 is another illustration of the tool of FIG. 1, showing various signals therein.

Referring now to FIG. 2, transmitter 12 is excited by an input voltage $V_0$, the power amplitude of the acoustic wave converted in the transducer element is $P_{10}=V_0 * K_{TC1}$, where $K_{TC1}$ is coupling factor of transmitter 12. The subsequent signal transmitted through the wall-fluid interface is thus given by $$P_{1T} = K_{TZ1} \cdot P_{10} = V_0 \cdot K_{TC1} \cdot K_{TZ1} \quad (1)$$

where the impedance factor $K_{TZ1} = 2Z_{f12} \cdot (Z_{f12} + Z_{w12})^{-1}$, where $Z_{f12}$ and $Z_{w12}$ are the acoustic impedances, respectively, of the fluid medium in the vicinity of transducer 12 and the conduit wall. If the fluid has an attenuation coefficient α, then the amplitude of the acoustic wave at some position r, is $P_{1s} = P_{1T} \cdot e^{-\alpha \cdot (R-r)}$, where r is the distance away from the center of the conduit and R is the conduit radius. Thus the amplitude of the attenuated wave reaching at the center, is $$P_{1s}(r=0) = P_{1T} \cdot e^{-\alpha \cdot R} = V_0 \cdot K_{TC1} \cdot K_{TZ1} \cdot e^{-\alpha \cdot R} \quad (2)$$

where R is the conduit radius. With the incident wave amplitude $P_{1s}$, the amplitude of the wave scattered by particulates located at the center of the conduit, is $$P_{r1s} = P_{1s} \cdot F \cdot (A \cdot \cos\theta_1 + B)^2 = V_0 \cdot K_{TC1} \cdot K_{TZ1} \cdot e^{-\alpha \cdot R} \cdot F \cdot (A \cdot \cos\theta_1 + B)^2 \quad (3)$$

where F is a factor related with the transmitting frequency and the particulate size. Factors A and B relate to the density ratio $\rho_s/\rho_f$ and the compressibility ratio $\beta_s/\beta_f$ of the particulate and the fluid medium phase as follows:

$$A \equiv \frac{3(1 - \rho_s/\rho_f)}{1 + 2\rho_s/\rho_f} \quad (4)$$

and $$B \equiv 1 - \frac{\beta_s}{\beta_f}. \quad (5)$$

Subscripts "s" and "f" in Equations (4) and (5) refer to the particulate and continuous fluid phase, respectively.

Taking into account the wave attenuation coefficient, the transmitted signal resulting from scattering of particulates at the conduit center, arriving at the wall-receiver 14 interface, is given by, $P_{r1w} = P_{r1s} \cdot e^{-\alpha \cdot R}$. The acoustic signal received by the receiver 14 is, $P_{r1} = P_{r1w} \cdot K_{RZ1}$, where the transmission coefficient at fluid-wall boundary, $K_{RZ1} = 2Z_{w14} \cdot (Z_{f14} + Z_{w14})^{-1}$, where, as above, $Z_{f14}$ and $Z_{w14}$ are the acoustic impedances of the fluid and wall near transducer 14. Therefore, considering the electro-mechanical coupling factor $K_{RC1}$ of the receiver 14, the power amplitude 38 of the scattered signals received by receiver as result of the signal emission from the transmitter 12 is expressed as $$P_{12-14} = V_0 \cdot K_{TC1} \cdot K_{TZ1} \cdot K_{RZ1} \cdot K_{RC1} \cdot e^{-2\alpha \cdot R} \cdot F \cdot (A \cdot \cos \theta_1 + B)^2 \quad (6)$$

Similarly, the power amplitude 40 of the scattered signals received by transducer 16 as result of the signal emitted by transducer 12 is given by $$P_{12-16} = V_0 K_{TC1} \cdot K_{TZ1} \cdot K_{RZ2} \cdot K_{RC2} \cdot e^{-2\alpha \cdot R} \cdot F \cdot (A \cdot \cos \theta_2 + B)^2 \quad (7)$$

Here $K_{RZ2} = 2Z_{w16} \cdot (Z_{f16} + Z_{w16})^{-1}$ is the transmission coefficient at the fluid-wall interface and $K_{RC2}$ is the electro-mechanical coupling factor for receiver 16.

Likewise, the power amplitude 42 of the scattered signals received by transducer 14 as result of signal emission from transducer 18 is given by:

$$P_{18-14} = V_0 K_{TC2} \cdot K_{TZ2} \cdot K_{RZ1} \cdot K_{RC1} \cdot e^{-2\alpha \cdot R} \cdot F \cdot [A \cdot \cos(\pi - \theta_1) + B]^2 \quad (8)$$

The power amplitude 44 of the scattered signals received by transducer 16 as result of signal emission from 18 is given by:

Arranging Equations (6)–(9), after canceling out the coupling factors, and impedance factors, frequency-related factors, and the attenuation factors, and letting $\Gamma = B/A$, gives $$\frac{P_{12-16} \cdot P_{18-14}}{P_{12-14} \cdot P_{18-16}} = \left[\frac{(\cos \theta_1 - \Gamma) \cdot (\cos \theta_2 + \Gamma)}{(\cos \theta_1 + \Gamma) \cdot (\cos \theta_2 - \Gamma)}\right]^2 \quad (10)$$

Since $\theta_1$ and $\theta_2$ are known, $\cos \theta_1$ and $\cos \theta_2$ are constants, and equation (10) can be solved for the dimensionless factor $\Gamma$, giving $$\Gamma = \frac{(\cos \theta_1 - \cos \theta_2) \cdot (1 + \varsigma) \pm \sqrt{(\cos \theta_1 - \cos \theta_2)^2 \cdot (1 + \varsigma)^2 + 4 \cdot (1 - \varsigma)^2 \cdot \cos \theta_1 \cdot \cos \theta_2}}{2 \cdot (1 - \varsigma)} \quad (11)$$

where $$\varsigma \equiv \left[\frac{P_{12-16} \cdot P_{18-14}}{P_{12-14} \cdot P_{18-16}}\right]^{1/2}.$$

Therefore, from the ratio of the measured power amplitudes of scattered signals, at the two different angles $\theta_1$ and $\theta_2$, the dimensionless factor $\Gamma$, which is a function of density and compressibility of the fluid system, can be determined. Because $\Gamma$ is based on the ratio of received signals between multiple pairs of transducers, it is not dependent on a quantitative measurement from any transducer. For this reason, it is not affected by any drift in the response of the transducers that may be caused by the changes in temperature or pressure. Similarly, the present system eliminates any error that might otherwise be caused by variations in individual transducer response due to electro-mechanical coupling, impedance variations associated with wall-fluid interfaces, frequency, driving signal voltage, and particulate size effects. For these reasons, the present system is sometimes referred to herein as "self-compensated."

The calculated value of $\Gamma$ determined from the compensated scattering measurement can be used to identify particulate/fluid medium systems. By way of example, Tables 1 and Table 2 list the values of $\Gamma$ for a few examples of suspended particulate/continuous liquid systems obtained at 25° C. and atmospheric pressure.

TABLE 1

Values of $\Gamma$ for particulate-in-water continuous fluids

|   | $CH_4$ gas bubbles in seawater | Crude oil droplets in seawater | Clay particles in seawater |
|---|---|---|---|
| $\Gamma$ | −6031 | −1.66 | −1.28 |

TABLE 2

Values of $\Gamma$ for particulate-in-oil continuous fluids

|   | $CH_4$ gas bubbles in crude oil | Seawater droplets in crude oil | Clay particles in crude oil |
|---|---|---|---|
| $\Gamma$ | −4516 | −1.33 | −1.12 |

While $\Gamma$ calculated in this manner can be used in conjunction with lookup tables or previous calibrations of the tool at known temperature and pressure conditions to provide quantitative information about the fluid being sampled, measurements of $\Gamma$ throughout a sampling period can give equally useful qualitative information about the fluid sampled during that period. In particular, in a given fluid sampling, it may be desirable to calculate $\Gamma$ every pulse repetition period (for example, for 10 KHz pulse repetition, every 100 microseconds) so that the change in $\Gamma$ over time can be observed.

For example, if the calculated value of $\Gamma$ begins with a value on the order of −1.28 and then shifts to a value on the order of −1.66, the change may be evidence of a change from solid particles to liquid droplets in seawater. A change from −1.66 at a first pressure $P_1$ to −6031 at a second pressure $P_2$ may be evidence that the bubble point pressure of the fluid is between $P_1$ and $P_2$. As individual $\Gamma$ values may vary for each pulse repetition time, statistical analysis of the $\Gamma$ values over many pulse repetitions provides more representative indication of the fluid characteristics.

Figure 3:
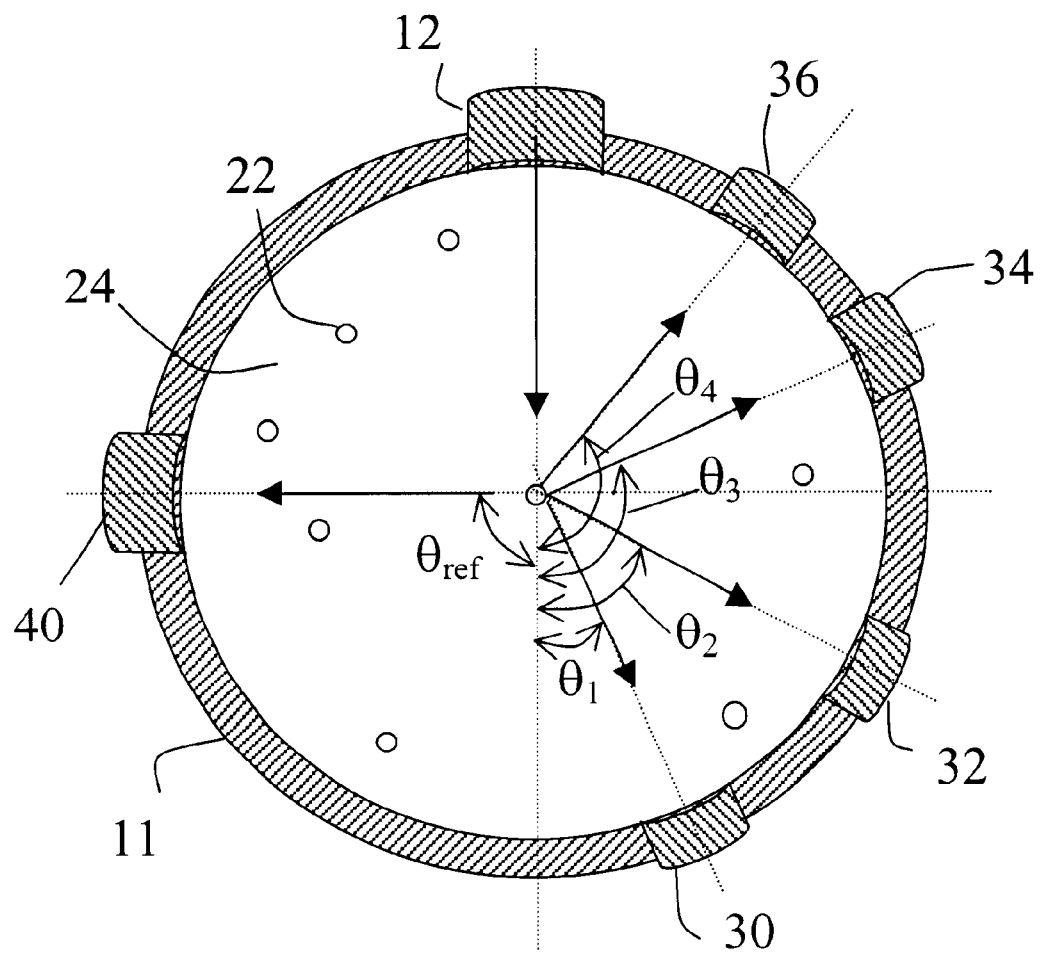
FIG. 3 is a schematic cross-section of a tool constructed in accordance with an alternative embodiment of the invention.

According to an alternative embodiment of the present invention, illustrated in FIG. 3, the fluid characteristics of continuous fluid medium and particulate inclusions can be identified from the angular dependence of scattering measured by multiple receivers at multiple azimuthal positions. By positioning receivers at different angles, the relative contributions of the density m factor A and the compressibility factor B to the measured scatter signal can be evaluated. As shown, a preferred angular scattering system comprises one transmitter 12, and five receivers 30, 32, 34, 36, and 40 positioned at different angles $\theta_1$, $\theta_2$, $\theta_3$, $\theta_4$, and $\theta_{ref}$, with respect to the incident wave direction. While the number of receivers may vary, it is preferred to have more than three receivers in order to sample as an wide angular range as possible. It is also preferred to position receivers in both the backward scattering region ($\pi/2 < \theta < \pi$, receivers 34 and 36 as shown) as well as in forward scattering region ($0 < \theta < \pi/2$, receivers 30 and 32 as shown). The amplitude of scatter signal measured at each receiver is normalized by the measured amplitude from a reference receiver (40) that is positioned for example at 90° degree with respect to the incident wave. Over the wide range of scattering angles, the normalized scattering power amplitude is:

$$\frac{P_i(\theta)}{P_{ref}(\theta_{ref})} = \left[\frac{\cos\theta_i + B/A}{\cos\theta_{ref} + B/A}\right]^2 \quad (12)$$

The scattering measurement can be thus calibrated and the dimensionless factor $\Gamma(=B/A)$ can be determined if the electromechanical coupling response due to each individual receiver (30, 32, 34, 36, 40) can been calibrated or known beforehand. By normalizing scattered signal $P_i$ from each receiver with the scattering signal amplitude of reference receiver $P_{ref}$, the terms related to incident wave amplitude, frequency, particle size, and wall-fluid impedance factors, can be cancelled.

Figure 4:
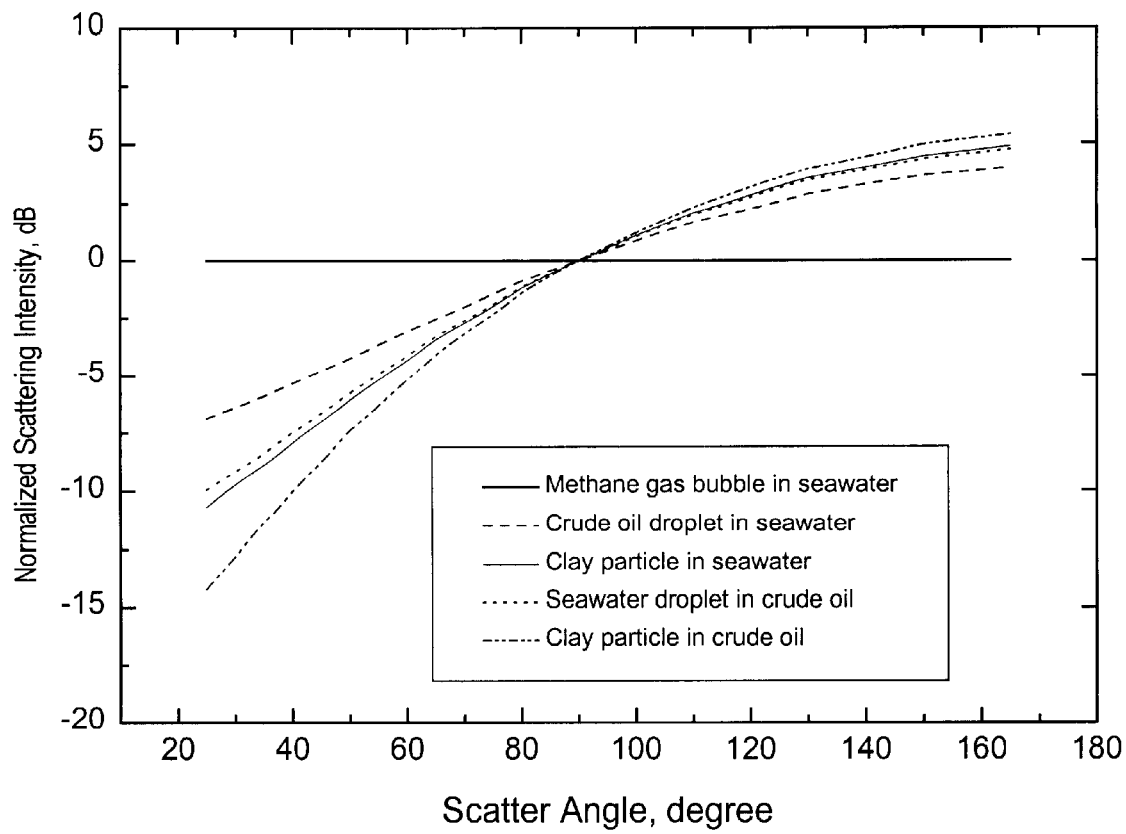
FIG. 4 is a plot of the calculated relative scattering intensity as function of scattering angle θ, for five different particulate-fluid systems.

Furthermore, angular dependence of the normalized scattering power amplitude $P_i/P_{ref}$ can be used to identify and monitor the fluid and particulate systems as well. As shown in FIG. 4, the calculated relative scattering intensity, $10*\log[P_i(\theta)/P_{ref}(\pi/2)]$, in unit of dB, are plotted as function of scattering angle $\theta$, for the five particulate-fluid systems of Table 1 and 2.

Figure 5:
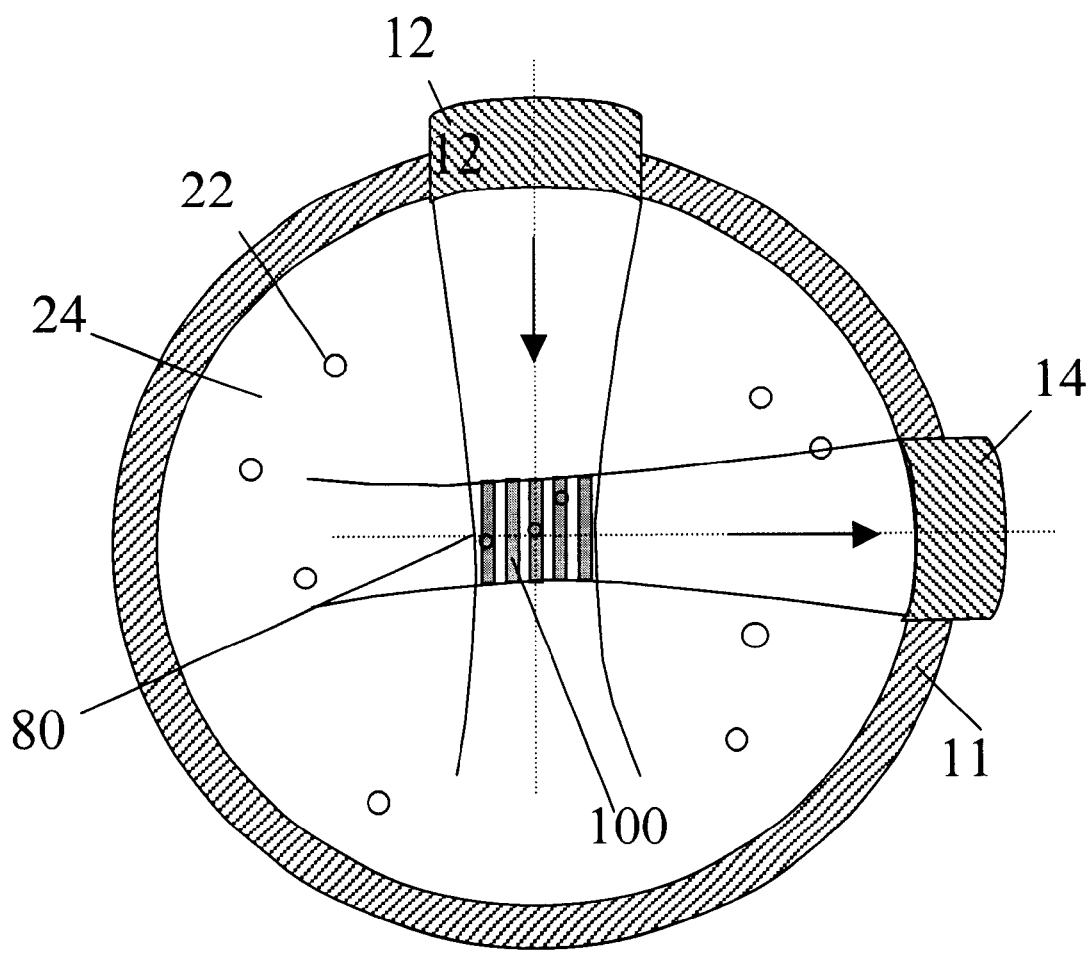
FIG. 5 is a schematic cross-section of a tool constructed in accordance with a second alternative embodiment of the invention and showing an alternative operation of the tool.

In yet another embodiment of the present invention, as illustrated in FIG. 5, the scattered signals received by the receiver 14 are time-gated to provide for finer spatial resolution of the sample. With speed of sound in the fluid known or determined separately, distances of each gated volumes from receiver 14 can be determined accurately based on their arrival times. Time-gating and analyzing of the scattered signals from each gated sample cell, can allow for determination of the fluid and particle characteristics as function of spatial distance. In a preferred embodiment, transmitter 12 and receiver 14 are mounted approximately perpendicularly, thus overlapping insonification region 80 is formed, and the subsequent time-gates are set so that sample cells 100 are substantially uniform in size.

The transmitter normally emits a pulse wave or a burst of sine waves at a very high repetition rate, such as from 10 kHz to 100 kHz. Thus electronic time-gating allows for analysis of the scattered echo profiles and measurement of variations in the fluid properties across the insonification volume, while fluid flows through the conduit. The scattered signal properties, i.e., the amplitude, phase, and the frequency components, for each gated scattered signal volume can be analyzed and compared with those for different radial depths (i.e., for each gated sample volume at a delay time) in the conduit. Variation in these scattered signal properties as function of time and radial distance can be monitored to allow for monitoring changes in the fluid characteristics such as variation of compressibility and density of the fluid flowing through the conduit.

ADVANTAGES

Advantages of the present self-compensated method and device include the ability to qualitatively monitor a fluid stream by identifying the type of the scattering particulate and the continuous fluid medium, the ability to distinguish the relative contribution of the density ratio A and the compressibility ratio B between the particulate and the continuous fluid medium to the angular scattering, and the ability to monitor these parameters without requiring re-calibration when the tool is subjected to variations in temperature or pressure. The present system also allows analysis of the quality of the fluid sample and the degree of contamination of the particulate phase. Because the present system allows detection and identification of gas bubbles, solid particles, or liquid droplets in a liquid medium, it can be used to detect and identify solid particles (clay, sand particles), liquid droplets (water or oil), and/or gas bubbles. This information may be utilized in various ways, including: forming the basis for a qualitative indication of the extent of drilling fluid contamination in formation fluid, allowing detection of gas vapor and gas bubbles and subsequent determination of bubble point pressure in formation fluids, and providing qualitative distinction between gas and liquid, water and oil, and crude oil and drilling mud fluid.

In addition to the uses described herein, the transmitters and receivers of the present invention can be calibrated and used in conjunction with look-up tables to give quantitative information, such as attenuation coefficient and speed of sound.

While a preferred embodiment of the present invention is described herein, it will be understood that various modifications to the method and apparatus can be made without departing from the scope of the present invention. For example, the number and position of the transducers can be varied. The receivers can be positioned at different azimuthal and axial positions with respect to the transmitter(s). Moreover, by directing and focusing acoustic beams, fluid properties at radial positions other than the conduit center may be monitored. Furthermore, the sequential recitation of steps in any claims is not a requirement that the steps be performed in any particular order, unless otherwise so stated.

What is claimed is:

1. A tool for using acoustical scattering measurements to measure fluid, comprising:
    a fluid container;
    first and second transmitters positioned in said container;
    first and second receivers positioned in said container, said receivers being differently azimuthally positioned with respect to said transmitters; and
    a data processor for receiving signals from said receivers, wherein said transmitters and said receivers are aligned such that a signal emitted by one of said first and second transmitters and scattered by the fluid under test is received by both the first and second receivers and the data processor uses the ratios of the signals from said first and second receivers to calculate a dimensionless parameter related to the density and compressibility of the fluid.

2. The tool according to claim 1 wherein the data processor uses the ratios of the signals from said first and second receivers to calculate a dimensionless parameter $\Gamma$ related to the density and compressibility of the fluid using the equation $$\Gamma = \frac{(\cos\theta_1 - \cos\theta_2)\cdot(1+\varsigma) \pm \sqrt{(\cos\theta_1 - \cos\theta_2)^2\cdot(1+\varsigma)^2 + 4\cdot(1-\varsigma)^2\cdot\cos\theta_1\cdot\cos\theta_2}}{2\cdot(1-\varsigma)}$$

where $\theta_1$ is the azimuthal position of the first receiver, where $\theta_2$ is the azimuthal position of the second receiver, and $\varsigma \equiv (P_{AD}\cdot P_{BC}/P_{AC}\cdot P_{BD})^{1/2}$ where $P_{AC}$ is the power amplitude of the signal received by said first receiver as result of the signal emitted by said first transmitter, $P_{AD}$ is the power amplitude of the signal received by said second receiver as result of the signal emitted by said first transmitter, $P_{BC}$ is the power amplitude of the signal received by said first receiver as result of the signal emitted by said second transmitter, and $P_{BD}$ is the power amplitude of the signal received by said second receiver as result of the signal emitted by said second transmitter.

3. The tool according to claim 1 wherein the fluid container comprises a conduit.

4. The tool according to claim 1, further including a third transmitter positioned in said container and a third receiver positioned in said container, said first, second and third receivers being differently azimuthally positioned with respect to said transmitters.

5. A method for analyzing a fluid using acoustical scattering measurements, comprising:

(a) positioning the fluid in a container that includes first and second transmitters and first and second receivers positioned therein, said first and second receivers being differently azimuthally positioned with respect to said transmitters;

(b) transmitting a first signal from the first transmitter and receiving the first signal at the first and second receivers as $P_{AC}$ and $P_{AD}$, respectively;

(c) transmitting a second signal from the second transmitter and receiving the second signal at the first and second receivers $P_{BC}$ and $P_{BD}$, respectively; and (d) using $P_{AC}$, $P_{AD}$, $P_{BC}$, and $P_{BD}$ to calculate a dimensionless parameter $\Gamma$ that is related to the density and compressibility of the fluid.

6. The method according to claim 5 wherein the fluid container comprises a conduit, further including the steps of flowing the fluid through the conduit and repeating steps (a)–(d) intermittently.

7. The method according to claim 6, further including the step of tracking changes in $\Gamma$ over time.

8. The method according to claim 6, further including the step of tracking changes in $\Gamma$ and using the changes to detect changes in the nature of the fluid.

9. The method according to claim 5 wherein step (d) includes calculating $\Gamma$ using the equation:

$$\Gamma = \frac{(\cos\theta_1 - \cos\theta_2)\cdot(1+\varsigma) \pm \sqrt{(\cos\theta_1 - \cos\theta_2)^2\cdot(1+\varsigma)^2 + 4\cdot(1-\varsigma)^2\cdot\cos\theta_1\cdot\cos\theta_2}}{2\cdot(1-\varsigma)}$$

where $\theta_1$ is the azimuthal position of the first receiver, where $\theta_2$ is the azimuthal position of the second receiver, and $\varsigma \equiv (P_{AD}\cdot P_{BC}/P_{AC}\cdot P_{BD})^{1/2}$ where $P_{AC}$ is the power amplitude of the signal received by said first receiver as result of the signal emitted by said first transmitter, $P_{AD}$ is the power amplitude of the signal received by said second receiver as result of the signal emitted by said first transmitter, $P_{BC}$ is the power amplitude of the signal received by said first receiver as result of the signal emitted by said second transmitter, and $P_{BD}$ is the power amplitude of the signal received by said second receiver as result of the signal emitted by said second transmitter.

10. The method according to claim 5 wherein the container farther includes a third transmitter and a third receiver positioned in said container, said first, second and third receivers being differently azimuthally positioned with respect to said transmitters.

11. A method for analyzing a fluid using acoustical scattering measurements, comprising:

(a) positioning the fluid in a container that includes a transmitter and at least first, second and third receivers positioned therein, said first, second and third receivers being each differently azimuthally positioned with respect to said transmitter at angles $\theta_1$, $\theta_2$, and $\theta_3$, respectively;

(b) transmitting a signal from the transmitter and receiving the signal at the first, second and third receivers as $P_1$, $P_2$, and $P_3$, respectively;

(c) normalizing the amplitude of the received signals $P_1$ and $P_2$ with respect to a reference received signal $P_3$; and (d) using $P_1$, $P_2$, and $P_3$ according to the equation $$\frac{P_i(\theta_i)}{P_3(\theta_{ref})} = \left[\frac{\cos\theta_i + B/A}{\cos\theta_3 + B/A}\right]^2$$

where $P_i$ is alternately $P_1$ and $P_2$ to calculate the relative contributions of the density factor A and the compressibility factor B to the measured signal.

12. The method according to claim 11, further including fourth and fifth receivers azimuthally positioned with respect to said transmitters at angles $\theta_4$ and $\theta_5$, wherein $\theta_4$ and $\theta_5$ are different from $\theta_1$, $\theta_2$ and $\theta_3$.

13. The method according to claim 11 wherein at least one receiver is positioned in each of the backward scattering region ($\pi/2 < \theta < \pi$) and the forward scattering region ($0 < \theta < \pi/2$).

14. The method according to claim 11, further including using the angular scattering dependence to identify and monitor fluid systems.

* * * * *